United States Patent [19]

Hilfman

[11] 4,061,563
[45] Dec. 6, 1977

[54] HYDROCRACKING OF HYDROCARBONS

[75] Inventor: Lee Hilfman, Mount Prospect, Ill.

[73] Assignee: UOP Inc., Des Plaines, Ill.

[21] Appl. No.: 716,922

[22] Filed: Aug. 23, 1976

Related U.S. Application Data

[60] Division of Ser. No. 599,561, July 28, 1975, Pat. No. 4,003,956, which is a continuation-in-part of Ser. No. 466,759, May 3, 1974, Pat. No. 3,931,048.

[51] Int. Cl.$^2$ .................. C10G 13/04; B01J 29/12
[52] U.S. Cl. .................. 208/111; 208/143; 208/216; 252/455 Z
[58] Field of Search ........... 208/111, 144, 143, 216, 208/255, 264

[56] References Cited

U.S. PATENT DOCUMENTS

| 2,999,074 | 9/1961 | Bloch et al. | 252/442 |
|---|---|---|---|
| 3,216,922 | 11/1965 | O'Hara | 208/111 |
| 3,472,791 | 10/1969 | Vesely | 252/448 |
| 3,668,114 | 6/1972 | O'Keefe et al. | 208/120 |
| 3,933,621 | 1/1976 | White et al. | 208/120 |

FOREIGN PATENT DOCUMENTS

| 1,183,778 | 3/1970 | United Kingdom | 208/111 |

*Primary Examiner*—Delbert E. Gantz
*Assistant Examiner*—G. E. Schmitkons
*Attorney, Agent, or Firm*—James R. Hoatson, Jr.; Thomas K. McBride; William H. Page, II

[57] ABSTRACT

A process for hydrotreating (hydroprocessing) hydrocarbons and mixtures of hydrocarbons utilizing a catalytic composite comprising a combination of a nickel component and a tungsten component with a silica-alumina carrier material wherein said carrier material is co-gelled silica-alumina consisting of from about 43 percent to about 57 percent by weight of alumina and from about 57 percent to 43 percent by weight silica and wherein said components are present in amounts sufficient to result in the composite containing, on an elemental basis, about 2 to about 10 percent by weight of the nickel component and about 8 to about 20 percent by weight of the tungsten component, in which process there is effected a chemical consumption of hydrogen. Key features of the subject composite are the criticality of the alumina content of the carrier material and the facility of using a co-gelled silica-alumina carrier material. The principal utility of the subject composite is in the hydrocracking of hydrocarbons. A specific example of the catalyst disclosed is a combination of nickel and tungsten with a co-gelled silica-alumina carrier material containing 50 weight percent alumina in amounts sufficient to result in the composite containing, on an elemental basis, about 7 to about 9 weight percent nickel and about 17 to about 19 weight percent tungsten. Other hydrocarbon hydroprocesses are directed toward the hydrogenation of aromatic nuclei, the ring-opening of cyclic hydrocarbons, desulfurization, denitrification, hydrogenation, etc.

3 Claims, 1 Drawing Figure

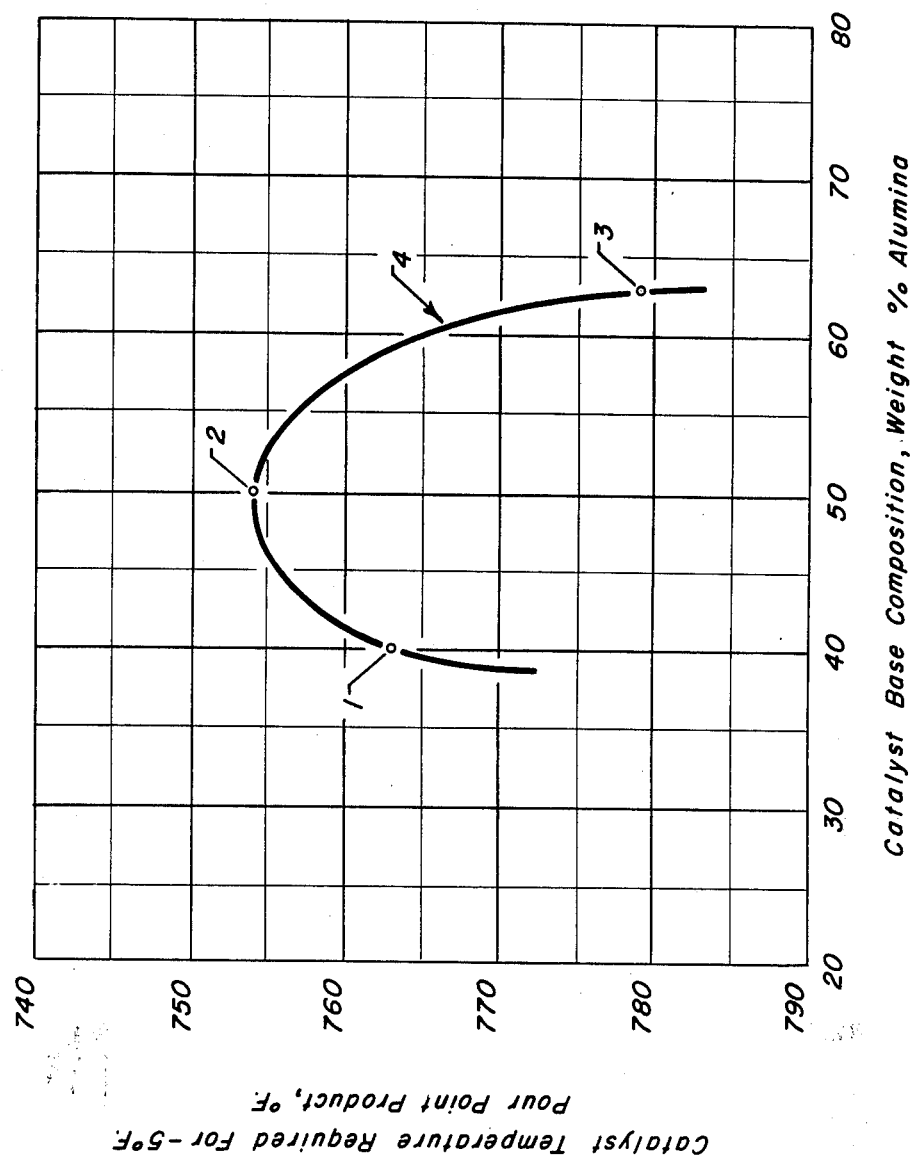

HYDROCRACKING OF HYDROCARBONS

CROSS-REFERENCE TO RELATED APPLICATIONS

The present application is a Division of my copending application, Ser. No. 599,561, filed July 28, 1975, now U.S. Pat. No. 4,003,956, issued Jan. 18, 1977, which is a Continuation-In-Part of application, Ser. No. 466,759, filed May 3, 1974, now U.S. Pat. No. 3,931,048, all the teachings of which applications are incorporated herein by specific reference thereto.

APPLICABILITY OF INVENTION

The present invention encompasses the use of a catalytic composite comprising a combination of a nickel component and a tungsten component with a silica-alumina carrier material wherein said carrier material is co-gelled silica-alumina consisting of from about 43 percent to about 57 percent by weight of alumina and from about 57 percent to 43 percent by weight silica and wherein said components are present in amounts sufficient to result in the composite containing on an elemental basis, about 2 to about 10 percent by weight of the nickel component and about 8 to about 20 percent by weight of the tungsten component in the hydrotreating of hydrocarbons and mixtures of hydrocarbons. As utilized herein, the term "hydrotreating" is intended to be synonymous with the term "hydroprocessing", which involves the conversion of hydrocarbons at operating conditions selected to effect a chemical consumption of hydrogen. Included within the processes intended to be encompassed by the term "hydroprocessing" are hydrocracking, aromatic hydrogenation, ring-opening, hydrorefining (for nitrogen removal and olefin saturation), desulfurization (often included in hydrorefining) and hydrogenation, etc. As will be recognized, one common attribute of these processes, and the reactions being effected therein, is that they are all "hydrogen-consuming", and are, therefore, exothermic in nature.

The individual characteristics of the foregoing hydrotreating processes, including preferred operating conditions and techniques, will be hereinafter described in greater detail. The subject of the present invention is the use of a catalytic composite which has exceptional activity and resistance to deactivation when employed in a hydrogen-consuming process. Such processes require a catalyst having both a hydrogenation function and a cracking function. More specifically, the present process uses a dual-function catalytic composite which enables substantial improvements in those hydroprocesses that have traditionally used a dual-function catalyst. The particular catalytic composite comprising a combination of a nickel component and a tungsten component with a silica-alumina carrier material wherein said carrier material is co-gelled silica-alumina consisting of from about 43 percent to about 57 percent by weight of alumina and from about 57 percent to 43 percent by weight silica and wherein said components are present in amounts sufficient to result in the composite containing, on an elemental basis, about 2 to about 10 percent by weight of the nickel component and about 8 to about 20 percent by weight of the tungsten component; specifically, an improved hydrocracking process utilizes a catalytic composite as hereinabove described for improved activity, product selectivity and operational stability characteristics.

Composites having dual-function catalytic activity are widely employed in many industries for the purpose of accelerating a wide spectrum of hydrocarbon conversion reactions. Generally, the cracking function is thought to be associated with an acid-acting material of the porous, adsorptive refractory inorganic oxide type which is typically utilized as the carrier material for a metallic component from the metals, or compounds of metals, of Groups V through VIII of the Periodic Table, to which the hydrogenation function is generally attributed.

Catalytic composites are used to promote a wide variety of hydrocarbon conversion reactions such as hydrocracking, isomerization, dehydrogenation, hydrogenation, desulfurization, reforming, ring-opening, cyclization, aromatization, alkylation and transalkylation, polymerization, cracking, etc., some of which reactions are hydrogen-producing while others are hydrogen-consuming. In using the term "hydrogen-consuming", I intend to exclude those processes wherein the only hydrogen consumption involves the saturation of light olefins, resulting from undesirable cracking, which produces the light paraffins, methane, ethane and propane. It is to the latter group of reactions, hydrogen-consuming, that the present invention is applicable. In many instances, the commercial application of these catalysts is in processes where more than one of these reactions proceed simultaneously. An example of this type of process is a hydrocracking process wherein catalysts are utilized to effect selective hydrogenation and cracking of high molecular weight materials to produce a lower-boiling, more valuable output stream. Another such example would be the conversion of aromatic hydrocarbons into jet fuel components, principally straight, or slightly branched paraffins.

Regardless of the reaction involved, or the particular process, it is very important that the catalyst exhibit not only the capability to perform its specified functions initially, but also perform them satisfactorily for prolonged periods of time. The analytical terms employed in the art to measure how efficient a particular catalyst performs its intended functions in a particular hydrocarbon conversion process, are activity, selectivity and stability. For the purpose of discussion, these terms are conveniently defined herein, for a given charge stock, as follows: (1) activity is a measure of the ability of the catalyst to convert a hydrocarbon feed stock into products at a specified severity level, where severity level alludes to the operating conditions employed — the temperature, pressure, liquid hourly space velocity and hydrogen concentration; (2) selectivity refers to the weight percent or volume percent of the reactants that are converted into the desired product and/or products; (3) stability connotes the rate of change of the activity and selectivity parameters with time — obviously, the smaller rate implying the more stable catalyst. With respect to a hydrogen-consuming process, for example hydrocracking, activity, stability and selectivity are similarly defined. Thus, "activity" connotes the quantity of charge stock, boiling above a given temperature, which is converted to hydrocarbons boiling below the given temperature. "Selectivity" refers to the quantity of converted charge stock which boils below the desired end point of the product, as well as above a minimum specified initial boiling point. "Stability" connotes the rate of change of activity and selectivity. Thus, for example, where a gas oil, boiling above about 650° F., is subjected to hydrocracking, "activity" connotes the conversion of 650° F.-pulse charge stock to 650° F.-minus product. "Selectivity" can allude to the quantity of conversion into gasoline boiling range hydrocarbons — i.e., pentanes and heavier, normally liquid hydrocarbons boiling up to about 400° F. "Stability" might be conveniently expressed in terms of temperature increase required during various increments of catalyst life, in order to maintain the desired activity.

As is well known to those skilled in the art, the principal cause of observed deactivation or instability of a dual-function catalyst is associated with the fact that coke forms on the surface of the catalyst during the course of the reaction. More specifically, in the various hydrocarbon conversion processes, and especially those which are categorized as hydrogen-consuming, the operating conditions utilized result in the formation of high molecular weight, black solid or semi-solid, hydrogen-poor carbonaceous material which coats the surface of the catalyst and reduces its activity by shielding its active sites from the reactants. Accordingly, a major problem facing workers in this area is the development of more active and selective catalytic composites that are not as sensitive to the presence of these carbonaceous materials and/or have the capability to suppress the rate of formation of these materials at the operating conditions employed in a particular process.

I have now found a dual-function catalyst composite which possesses improved activity, selectivity and stability when employed in the hydroprocessing of hydrocarbons, wherein there is effected a chemical consumption of hydrogen. In particular, I have found that the use of a catalytic composite comprising a combination of a nickel component and a tungsten component with a silica-alumina carrier material wherein said carrier material is co-gelled silica-alumina consisting of from about 43 percent to about 57 percent by weight of alumina and from about 57 percent to 43 percent by weight silica and wherein said components are present in amounts sufficient to result in the composite containing, on an elemental basis, about 2 to about 10 percent by weight of the nickel component and about 8 to about 20 percent by weight of the tungsten component improves the overall operation of these hydrogen-consuming processes. Moreover, I have determined that a catalytic composite as hereinabove described, when untilized in a process for hydrocracking hydrocarbonaceous material into lower-boiling hydrocarbon products, affords substantial improvement in performance and results. As indicated, the present invention essentially enables the performance characteristics of the process to be sharply and materially improved.

Destructive hydrogenation by catalytic means, more commonly called hydrocracking, is old and well-known to the art. Destructive hydrogenation of the hydrocarbon oil, which is usually a coal tar or a high-boiling petroleum fraction, such as gas oils or topped crude, generally is performed at relatively high temperatures and pressures of the order of 750° F. and 1500 psig., and upward. Catalysts for the destructive hydrogenation of hydrocarbons are generally a combination of hydrogenation and cracking catalysts.

While many types of catalyst compositions have been proposed for destructive hydrogenation or hydrocracking, it has been found that catalysts comprised of silica, alumina, tungsten and nickel are especially suitable. Such catalysts are well known in the hydrocracking art.

From U.S. Pat. No. 3,216,922, a process is known for the preparation of hydrocracking catalysts comprising a silica-alumina mixture as a carrier in which the carrier is obtained by first precipitating silica gel from a water glass solution and subsequently, after aging of the gel, precipitating aluminum hydroxide thereon. As the aluminum salt from which the aluminum hydroxide is formed, use is made of aluminum sulphate which is added in such a quantity that the molar ratio of silica to alumina in the finished carrier is approximately 5:1. It was found, however, that the use of hydrocracking catalysts, of which the carrier was obtained in the manner described, produced less favorable results in the hydrocracking of flashed distillates.

In an effort to prepare a more satisfactory hydrocracking catalyst, British Patent No. 1,183,778 teaches a process for the preparation of an alumina-silica-nickel-tungsten hydrocracking catalyst which comprises preparing a catalyst carrier by first precipitating from an aqueous solution comprising silicate ions, a silica gel, subjecting the gel to aging at elevated temperature, precipitating aluminum hydroxide on the aged gel by addition of an aqueous aluminum nitrate solution and an alkaline-reacting solution, separating, drying and finally calcining the resulting precipitate of aluminum hydroxide on silica gel and then supporting tungsten and nickel on the catalyst carrier and subsequently oxidizing the carrier comprising the metal salts.

However, because commercial scale hydrocracking of hydrocarbons is performed at low space velocities, catalyst cost is an appreciable factor in both the initial investment and operating costs of hydrocracking plants. For this reason, there is considerable incentive to manufacture such catalysts by the most economic method while improving the catalyst activity. I have discovered an improved process for the preparation of tungsten-nickel on silica-alumina hydrocracking catalyst.

More specifically, I have found that a co-gelled silica-alumina is an exceptionally suitable carrier material. A co-gelled silica-alumina carrier material in addition to being catalytically suitable is more simply and economically produced than the prior are carriers. The production of prior art carriers has been a multi-step process which has required the expenditure of time and effort far in excess of that required for a co-gelled carrier.

More specifically, my process is an improved process for the preparation of such catalyst wherein the nickel component is present in an amount from about 2 weight percent to about 10 weight percent, and the tungsten component is present in an amount from about 8 weight percent to 20 weight percent. I have also discovered that an unusually superior catalyst results if the catalyst base contains from about 43 percent to about 57 percent by weight of alumina. The criticality of the range of the alumina concentration is further illustrated hereinbelow.

A particularly preferred co-gelled silica-alumina catalyst base comprises from about 43 percent to about 57 percent alumina and from about 57 percent to about 43 percent silica and still more preferably from about 48 percent to about 52 percent alumina.

In addition to the foregoing compositional limitations, it is important that the catalyst base have adequate pore volume, that is, a pore volume of at least 0.5 cc./g. and preferably at least 0.6 cc./g. or even 0.7 cc./g.

The co-gelled silica-alumina catalyst base is preferably in the xerogel state, that is, it is dried sufficiently to afford the usual microporous structure and therefore an appreciable available surface. It is also possible to use a rigid silica-alumina catalyst base which has merely been dried at a relatively low temperature, e.g., 125° C., and which still contains considerable amounts of water. In this latter case, however, the degree of drying must nevertheless be sufficient to remove essentially all water from the pores of the base.

The catalyst of the present invention can be utilized to achieve the maximum production of LPG (liquefied petroleum gas) in the propane/butane range from naphtha or gasoline boiling range distillates. Heavier charge stocks, including kerosenes, light gas oils, heavy gas oils, full boiling range gas oils and "black oils" may be readily converted into lower-boiling, normally liquid products including gasolines, kerosenes, middle-distillates, lube oils, etc.

In one embodiment, accordingly, the present invention provides a method of preparing catalysts having hydrocracking activity comprising the steps: (a) co-gelling a silica-alumina carrier material consisting of from about 43 percent to about 57 percent by weight alumina and from about 57 to 43 percent by weight silica; (b) impregnating said silica-alumina carrier material with an aqueous solution of a nickel salt and a tungsten salt, the concentrations of the salts in the aqueous solution being sufficient to deposit on the carrier material an amount of salts equivalent to 2 to 10 percent by weight nickel and 8 to 20 percent by weight tungsten based on the total weight of the finished catalyst; and, (c) calcining the impregnated carrier material.

In a second embodiment, the present invention relates to a process for hydrocracking hydrocarbons which process comprises reacting said hydrocarbons with hydrogen in a reaction zone containing a catalytic composite prepared by a method comprising the steps: (a) co-gelling a silica-alumina carrier material consisting of from about 43 percent to about 57 percent by weight alumina and from about 57 to 43 percent by weight silica; (b) impregnating said silica-alumina carrier material with an aqueous solution of a nickel salt and a tungsten salt, the concentrations of the salts in the aqueous solution being sufficient to deposit on the carrier material an amount of salts equivalent to 2 to 10 percent by weight nickel and 8 to 20 percent by weight tungsten based on the total weight of the finished catalyst; and, (c) calcining the impregnated carrier material.

In a specific embodiment, the hydrocracking conditions include a maximum catalyst bed temperature of about 600° F. to about 900° F., a pressure of about 500 to about 5000 psig., a liquid hourly space velocity of about 0.1 to about 10 and a hydrogen circulation rate in the range of about 1,000 to about 50,000 scf./bbl.

In another specific embodiment, the catalytic composite is oxidized, in an atmosphere of air, at a temperature about 1000° F. prior to contact with the fresh feed charge stock.

Another embodiment relates to a catalytic composite, comprising a combination of a nickel component and a tungsten component with a silica-alumina carrier material wherein said carrier material is cogelled silica-alumina consisting of from about 43 percent to about 57 percent by weight alumina and from about 57 percent to 43 percent by weight silica and wherein said components are present in amounts sufficient to result in the composite containing; on an elemental basis, about 2 to about 10 percent by weight of the nickel component and about 8 to about 20 percent by weight of the tungsten component.

An object of the present invention is to afford a process for the hydroprocessing of a hydrocarbon, or mixture of hydrocarbons. A corollary objective is to improve the selectivity and stability of hydroprocessing utilizing a highly active catalytic composite of the present invention.

A specific object of my invention resides in the improvement of hydrogen-consuming processes including hydrocracking, hydrorefining, ring-opening for jet fuel production, hydrogenation or aromatic hydrocarbons, desulfurization, denitrification, etc. Therefore, in one embodiment, the present invention encompasses a hydrocarbon hydroprocess which comprises reacting a hydrocarbon with hydrogen at conditions selected to effect chemical consumption of hydrogen and in contact with a catalytic composite as hereinabove described. In another embodiment, the operating conditions include a pressure of from 400 to about 5,000 psig., an LHSV (defined as volumes of liquid hydrocarbon charge per hour per volume of catalyst disposed in the reaction zone) of from 0.1 to about 10.0, a hydrogen circulation rate of from 1,000 to about 50,000 scf./Bbl. and a maximum catalyst temperature of from 200° F. to about 900° F.

In another embodiment, the process is further characterized in that the catalytic composite is reduced and sulfided prior to contacting the hydrocarbon feed stream. In still another embodiment, my invention involves a process for hydrogenating a coke-forming hydrocarbon distillate containing di-olefinic and mono-olefinic hydrocarbons, and aromatics, which process comprises reacting said distillate with hydrogen, at a temperature below about 500° F., in contact with a catalytic composite comprising a combination of a nickel component and a tungsten component with a silica-alumina carrier material wherein said carrier material is co-gelled silica-alumina consisting of from about 43 percent to about 57 percent by weight of alumina and from about 57 percent to 43 percent by weight silica and wherein said components are present in amounts sufficient to result in the composite containing, on an elemental basis, about 2 to about 1 percent by weight of the nickel component and about 8 to about 20 percent by weight of the tungsten component and an alkali metal component, and recovering an aromatic/-mono-olefinic hydrocarbon concentrate substantially free from conjugated di-olefinic hydrocarbons.

Another embodiment affords a catalytic composite comprising a substantially pure crystalline aluminosilicate material, at least about 90.0% by weight of which is zeolitic.

Other objects and embodiments of my invention relate to additional details regarding preferred catalytic ingredients, the concentration of components in the catalytic composite, methods of catalyst preparation, individual operating for use in the various hydrotreating processes, preferred processing techniques and the like particulars which are hereinafter given in the following more detailed summary of my invention.

As hereinabove set forth, the present invention involves the hydroprocessing of hydrocarbons and mixtures of hydrocarbons, utilizing a particular catalytic composite. This catalyst comprises a combination of a nickel component and a tungsten component with a silica-alumina carrier material wherein said carrier material is co-gelled silica-alumina consisting of from about 43 percent to about 57 percent by weight of alumina and from about 57 percent to 43 percent by weight silica and wherein said components are present in amounts sufficient to result in the composite containing, on an elemental basis, about 2 to about 1 percent by weight of the nickel component and about 8 to about 20 percent by weight of the tungsten component.

Catalytic composites, tailored for the conversion of hydrocarbonaceous material and particularly those intended for utilization in a hydrocracking process, have traditionally consisted of metallic elements chosen from Group VIII of the Periodic Table; however, metallic components from Group VI-B are quite often incorporated therein. In those instances where hydrocracking is intended to be accompanied by some hydrorefining (desulfurization, denitrification, etc.) the preferred metallic components have been nickel and molybdenum, and nickel and tungsten, which components are usually combined with a porous carrier material comprising both alumina and silica, either amorphous or zeolitic in nature. Ample evidence may be found in the literature which confirms the ability of the nickel component to effect both cracking and hydrogenation reactions. Furthermore, the prior art indicates a preference for two particular methods of catalyst preparation. Predominantly preferred is an impregnating procedure wherein a previously calcined, preformed carrier material, which is precipitated in a multi-step manner as hereinabove described, is contacted with suitable soluble compounds of the nickel component and the Group VI-B component, where the latter is utilized. Impregnation involves both subsequent drying at a temperature of about 300° F., and oxidation at a temperature of about 1100° F. The second preferred preparation scheme involves coprecipitating all the catalyst components, including those of the carrier material.

I have found that a particularly effective silica-alumina-nickel-tungsten hydrocracking catalyst can be prepared when the alumina content of the co-gelled silica-alumina support is maintained within the critical range of from about 43 percent to about 57 percent by weight alumina. Thus, it is now possible to prepare a more active and stable hydrocracking catalyst.

As is customary in the art of catalysis, when referring to the catalytically active metal, or metals, it is intended to encompass the existence of such metal in the elemental state or in some form such as an oxide, sulfide, halide, etc. Regardless of the state in which the metallic components actually exist, the concentrations are computed as if they existed in the elemental state.

The co-gelled silica-alumina may be prepared and utilized as spheres, pills, pellets, extrudates, granules, etc. In a preferred method of manufacture, an aqueous water glass solution, diluted to a silica concentration of from about 5 to about 15 weight percent, is acidified with hydrochloric acid or other suitable mineral acid. The resulting sol is acid aged at a pH of from about 4 to about 4.8 to form a hydrogel, and the hydrogel is further aged at a pH of from about 6.5 to about 7.5. The silica hydrogel is then thoroughly admixed with an aqueous aluminum salt solution of sufficient concentration to provide a desirable alumina content in the silica-alumina product. The silica-alumina sol is then precipitated at a pH of about 8 by the addition of a basic precipitating agent, suitably aqueous ammonium hydroxide. The silica-alumina, which exists as a hydrogel slurried in a mother liquor, is recovered by filtration, water-washed and dried at a temperature of from about 200° to about 500° F. Drying is preferably by spray-drying techniques whereby the co-gelled silica-alumina is recovered as microspheres, admixed with a suitable binding agent, such as graphite, polyvinyl alcohol, etc., and extruded or otherwise compressed into pills or pellets or uniform size and shape.

The particularly preferred method for preparing the co-gelled silica-alumina support is by the well known oil-drop method which permits the utilization of the support in the form of macrospheres. For example, an alumina sol, utilized as an alumina source, is commingled with an acidified water glass solution as a silica source, and the mixture further commingled with a suitable gelling agent, for example, urea, hexamethylenetetramine, or mixtures thereof. The mixture is discharged while still below gellation temperature, and by means of a nozzle or rotating disk, into a hot oil bath maintained at gellation temperature. The mixture is dispersed into the oil bath as droplets which form into spheriodal gel particles during passage therethrough. The alumina sol is preferably prepared by a method wherein aluminum pellets are commingled with a quantity of treated or deionized water, with hydrochloric acid being added thereto in a sufficient amount to digest a portion of the aluminum metal and form the desired sol. A suitable reaction rate is effected at about reflux temperature of the mixture.

The spheroidal gel particles prepared by the oil-drop method are aged, usually in the oil bath, for a period at least 10–16 hours, and then in a suitable alkaline or basic medium for at least 3 to about 10 hours, and finally water-washed. Proper gellation of the mixture in the oil bath, as well as subsequent aging of the gel spheres, is not readily accomplished below about 120° F., and at about 210° F., the rapid evolution of the gases tends to rupture and otherwise weaken the spheres. By maintaining sufficient superatmospheric pressure during the forming and aging steps in order to maintain water in the liquid phase, a higher temperature can be employed, frequently with improved results. If the gel particles are aged at superatmospheric pressure, no alkaline aging step is required.

The spheres are water-washed, preferably with water containing a small amount of ammonium hydroxide and/or ammonium nitrate. After washing, the spheres are dried, at a temperature of from about 200° F. to about 600° F. for a period of from about 6 to about 24 hours or more, and then calcined at a temperature of from about 800° to about 1400° F. for a period of from about 2 to about 12 hours or more.

The nickel component and the tungsten component are composited with the co-gelled silica-alumina carrier material by any suitable co-impregnation technique. Thus, the carrier material can be soaked, dipped, suspended, or otherwise immersed in an aqueous impregnating solution containing a soluble nickel salt and a soluble tungsten salt. One suitable method comprises immersing the carrier material in the impregnating solution and evaporating the same to dryness in a rotary steam dryer, the concentration of the impregnating solution being such as to ensure a final catalyst composite comprising from about 2 to about 10 percent by weight nickel and 8 to about 20 percent by weight tungsten.

The catalyst composite is usually dried at a temperature of from about 200° to about 500° F. for a period of from about 1 to about 10 hours prior to calcination. In accordance with present invention, calcination is effected in an oxidizing atmosphere at a temperature of from about 700° to about 1200° F. The oxidizing atmosphere is suitably air, although other gases comprising molecular oxygen may be employed.

Following the high temperature oxidation procedure the catalyst is usually reduced for a period of from about one-half to about 10 hours at a temperature in the range of from about 700° F. to about 1000° F. in the presence of hydrogen. The catalyst may be used in a sulfided form. Thus after reduction, the catalyst may be subjected to sulfidation by passing hydrogen sulfide, or other suitable sulfur containing compound, in contact therewith, preferably at an elevated temperature of from about 500° F. to about 1100° F. The reduced catalyst is preferably sulfided by contacting the catalyst with a stream by hydrogen containing from about 1 to 20 percent or more by volume of hydrogen sulfide at elevated temperatures of from about 500° F. to about 1100° F. When the petroleum hydrocarbon to be hydrocracked contains sulfur compounds, by design or otherwise, sulfidation may be suitably effected in situ in the initial stages of the hydrocracking process.

The catalyst composite, prepared in accordance with the method of this invention, is preferably employed in a reaction zone as a fixed bed. The hydrocarbon charge stock after being combined with hydrogen in an amount of from about 2000 to about 20,000 standard cubic feet per barrel, and preferably at least about 5000 standard cubic feet per barrel, is introduced into the reaction zone. The charge stock may be in a liquid, vapor or liquid-vapor phase mixture, depending upon the temperature, pressure, proportion of hydrogen and the boiling range of the charge stock being processed. The liquid hourly space velocity through the reaction zone will be in excess of about 0.2 and generally in the range of from about 1.0 to about 15.0. The source of hydrogen being admixed with a hydrocarbon charge stock may comprise a hydrogen-rich gas stream which is withdrawn from a high-pressure, low-temperature separation zone and recycled to supply at least a portion of such hydrogen. Excess hydrogen resulting from the various dehydrogenation reactions effected in a catalytic reforming unit may also be employed in admixture with the hydrocarbon charge. The reaction zone will operate under an imposed pressure within the range of from about 80 to about 3000 pounds per square inch gauge. The catalyst bed inlet temperature is maintained within the range of from about 350° to about 800° F. Since the hydrocracking reactions are exothermic, the outlet temperature or the temperature at the bottom of the catalyst bed will be significantly higher than that at the inlet thereto. The degree of exothermicity exhibited by the temperature rise across the catalyst bed is at least partially dependent upon the character of the charge stock passing therethrough, the rate at which the normally liquid hydrocarbon charge contacts the catalyst bed, the intended degree of conversion to lower-boiling-hydrogen products, etc. In any event, the catalyst bed inlet temperature will be such that the exothermicity of the reactions taking place does not cause the temperature at the outlet of the bed to exceed about 900° F., and preferably 850° F. The operation may also be effected as a moving-bed type, or suspensoid type of operation in which the catalyst, hydrocarbon and hydrogen are admixed and passed as a slurry through the reaction zone.

Although the method of preparing the catalyst, and careful selection of operating conditions within the ranges hereinbefore set forth, extend the effective life of the catalyst composite, regeneration thereof may eventually become desired due to the natural deterioration of the catalytically active metallic components. The catalyst composite is readily regenerated by treating the same in an oxidizing atmosphere, at a temperature of from about 750° to about 850° F., and burning coke and other heavy hydrocarbonaceous material therefrom. The catalyst composite may then be subjected to the reducing action in hydrogen, in situ, at a temperature within the range of from about 1000° to about 1200° F. If desirable, the catalyst may then be sulfided in the same manner as fresh catalyst as hereinbefore described.

Although not essential to successful hydroprocessing in all cases, in fact detrimental in some, a halogen component may be incorporated into the catalyst composite. Accordingly, a preferred catalyst composite, for use in the present process, comprises a combination of a nickel component and a tungsten component with a silica-alumina carrier material wherein said carrier material is co-gelled silica-alumina consisting of from about 43 percent to about 57 percent by weight alumina and from about 57 percent to 43 percent by weight silica and wherein said components are present in amounts sufficient to result in the composite containing, on an elemental basis, about 2 to about 10 percent by weight of the nickel component and about 8 to about 20 percent by weight of the tungsten component and a halogen component. Although the precise form of the chemistry of the association of the halogen component with the carrier material and metallic components is not accurately known, it is customary in the art to refer to the halogen component as being combined with the carrier material, or with the other ingredients of the catalyst. The combined halogen may be either fluorine, chlorine, iodine, bromine, or mixtures thereof. Of these fluorine and particularly chlorine are preferred for the hydrogen hydroprocesses encompassed by the present invention. The halogen may be added to the carrier material in any suitable manner, and either during preparation of the carrier or before, or after the addition of the other components. For example, the halogen may be added at any stage of the preparation of the carrier material, or to the calcined carrier material, as an aqueous solution of an acid such as hydrogen fluoride, hydrogen chloride, hydrogen bromide, hydrogen iodide, etc. The halogen component or a portion thereof may be composited with the carrier material during the impregnation of the latter with the metal components. The inorganic oxide hydrosol, which is typically utilized to form an amorphous carrier material, may contain halogen and thus contribute at least a portion of the halogen component to the final composite. The quantity of halogen is such that the final catalytic composite contains about 0.1% to about 1.5% by weight, and preferably from about 0.5% to about 1.2%, calculated on an elemental basis.

In embodiments of the present invention wherein the instant catalyst composite is used for the hydrogenation of hydrogenatable hydrocarbons, it is ordinarily a preferred practice to include an alkaline earth metal component in the composite. More precisely, this optional component is selected from the group consisting of the compounds of the alkali metals — cesium, rubidium, potassium, sodium, and lithium — and the compounds of the alkaline earth metals — calcium, strontium, barium and magnesium. Generally, good results are obtained in these embodiments when this component constitutes about 1 to about 5 weight percent of the composite, calculated on an elemental basis. This optional alkali or alkaline earth metal component can be incorporated in the composite in any of the known ways, with impregnation with an aqueous solution of a suitable water-soluble, decomposable compound being preferred.

An optional ingredient for the catalyst of the present invention is a Friedel-Crafts metal halide component. This ingredient is particularly useful in hydrocarbon conversion embodiments of the present invention wherein it is preferred that the catalyst utilized has a strong acid or cracking function associated therewith — for example, an embodiment wherein hydrocarbons are to be hydrocracked or isomerized with the catalyst of the present invention. Suitable metal halides of the Friedel-Crafts type include aluminum chloride, aluminum bromide, ferric chloride, ferric bromide, zinc chloride and the like compounds, with the aluminum halides and particularly aluminum chloride ordinarily yielding best results. Generally, this optional ingredient can be incorporated into the composite of the present invention by any of the conventional methods for adding metallic halides of this type; however, best results are ordinarily obtained when the metallic halide is sublimed onto the surface of the carrier material according to the preferred method disclosed in U.S. Pat. No. 2,999,074. The component can generally be utilized in any amount which is catalytically effective, with a value selected from the range of about 1 to about 100 wt. % of the carrier material generally being preferred. When used in many of the hydrogen-consuming processes hereinbefore described, the foregoing quantities of metallic components will be combined with a carrier material of alumina and silica, wherein the silica concentration is 10.0% to about 90.0% by weight.

Regardless of the details of how the components of the catalyst are combined with the porous carrier material, the final catalyst generally will be dried at a temperature of from about 200° to about 600° F. for a period of at least about 2 to about 24 hours or more, and finally calcined or oxidized at a temperature of about 700° F. to about 1100° F. in an air atmosphere for a period of about 0.5 to about 10 hours. Because a halogen component may be utilized in the catalyst, best results are generally obtained when the halogen content of the catalyst is adjusted during the calcination step by including a halogen or a halogen-containing compound in the air atmosphere utilized. In particular, when the halogen component of the catalyst is chlorine, it is preferred to use a mole ratio of $H_2O$ to HCl of about 5:1 to about 100:1 during at least a portion of the calcination step in order to adjust the final chlorine content of the catalyst to a range of about 0.5 to about 1.5 weight percent.

The resulting reduced catalytic composite may, in some cases, be beneficially subjected to a presulfiding operation designed to incorporate in the catalytic composite from about 0.05 to about 0.5 weight percent sulfur calculated on an elemental basis. Preferably, this presulfiding treatment takes place in the presence of hydrogen and a suitable sulfur-containing compound such as hydrogen sulfide, lower molecular weight mercaptans, organic sulfides, etc. Typically, this procedure comprises treating the selectively reduced catalyst with a sulfiding gas such as a mixture of hydrogen and hydrogen sulfide having about 10 moles of hydrogen per mole of hydrogen sulfide at conditions sufficient to effect the desired incorporation of sulfur, generally including a temperature ranging from about 50° F. up to about 1100° F. or more. It is generally a good practice to perform this presulfiding step under substantially water-free conditions.

According to the present invention, a hydrocarbon charge stock and hydrogen are contacted with a catalyst of the type described above in a hydrocarbon conversion zone. This contacting may be accomplished by using the catalyst in a fixed bed system, a moving bed system, a fluidized bed system, or in a batch type operation; however, in view of the danger of attrition losses of the valuable catalyst and of well known operational advantages, it is preferred to use a fixed bed system. In this system, a hydrogen-rich gas and the charge stock are preheated by any suitable heating means to the desired reaction temperature and then are passed, into a conversion zone containing a fixed bed of the catalyst type previously characterized. It is, of course, understood that the conversion zone may be one or more separate reactors with suitable means therebetween to insure that the desired conversion temperature is maintained at the entrance to each reactor. It is also important to note that the reactants may be contacted with the catalyst bed in either upward, downward, or radial flow fashion with the latter being preferred. In addition, the reactants may be in the liquid phase, a mixed liquid-vapor phase, or a vapor phase when they contact the catalyst.

The operating conditions imposed upon the reaction zone are dependent upon the particular hydroprocessing being effected. However, these operating conditions will include a pressure from about 400 to about 5000 psig., a liquid hourly space velocity of about 0.1 to about 10.0, and a hydrogen circulation rate within the range of about 1,000 to about 50,000 standard cubic feet per barrel. In view of the fact that the reactions being effected are exothermic in nature, an increasing temperature gradient is experienced as the hydrogen and feed stock traverses the catalyst bed. For any given hydrogen-consuming process, it is desirable to maintain the maximum catalyst bed temperature below about 900° F., which temperature is virtually identical to that conveniently measured at the outlet of the reaction zone. Hydrogen-consuming processes are conducted at a temperature in the range of about 200° F. to about 900° F., and it is intended herein that the stated temperature of operation alludes to the maximum catalyst bed temperature. In order to assure that the catalyst bed temperature does not exceed the maximum allowed for a given process, the use of conventional quench streams, either normally liquid or gaseous, introduced at one or more intermediate loci of the catalyst bed, may be utilized. In some of the hydrocarbon hydroprocesses encompassed by the present invention, and especially where hydrocracking a heavy hydrocarbonaceous material to produce lower-boiling hydrocarbon products, that portion of the normally liquid product effluent boiling above the end point of the desired product will be recycled to combine with the fresh hydrocarbon charge stock. In these situations, the combined liquid feed ratio (defined as volumes of total liquid charge to the reaction zone per volume of fresh feed charge to the reaction zone) will be within the range of about 1.1 to about 6.0.

The drawing included in the instant application is for the purpose of visually demonstrating the improvements and advantages afforded by the manufacture of silica-alumina-nickel-tungsten hydrocracking catalyst according to the present invention.

The following example is presented in illustration of the catalyst of this invention and a method of preparation thereof, and is not intended as an undue limitation on the generally broad scope of the invention as set out in the appended claims.

EXAMPLE I

This example described the preparation and testing of three silica-alumina-nickel-tungsten catalysts each of which contains 8% nickel and 18% tungsten and which contain 40, 50 and 63 weight percent alumina, respectively. The co-gelled silica-alumina support material for each catalyst was prepared by the hereinabove described oil-drop method and the ratio of silica and alumina sources was selected to yield a finished support material which had the desired alumina content. The finished support material was in the form of 1/16 inch spheres.

A batch of co-gelled support material containing 40 weight percent alumina was impregnated with an aqueous solution of nickel nitrate and ammonium metatungstate. The impregnated spheres were dried and then oxidized at a temperature of 1100° F. The concentration of the metal salts in the aqueous impregnation solution was selected to yield a finished catalyst which contained 8 weight percent nickel and 18 weight percent tungsten. This batch of finished hydrocracking catalyst will hereinafter be referred to as catalyst 1.

A batch of co-gelled support material containing 50 weight percent alumina was then used to prepare catalyst 2 in the same manner as catalyst 1. Catalyst 2 also contained 8 weight percent nickel and 18 weight percent tungsten.

A batch of co-gelled support material which contained 63 weight percent alumina was impregnated to yield a finished catalyst 3 containing 8 weight percent nickel and 18 weight percent tungsten in exactly the same manner as the two previous preparations.

Each of the catalysts prepared in this manner were then used in the hydrocracking of a light vacuum gas oil whose properties are summarized in Table I.

TABLE I

| Properties of Light Vacuum Gas Oil | |
|---|---|
| API° Gravity at 60° F. | 36.7 |
| Specific Gravity at 60° F. | 0.8413 |
| Distillation, ° F. | |
| IBP | 550 |
| 10 | 635 |
| 30 | 688 |
| 50 | 716 |
| 70 | 742 |
| 90 | 785 |
| E.P. | 856 |
| Total Sulfur, wt. % | 0.07 |
| Total Nitrogen, wt. % | 0.044 |
| Aromatics, vol. % | 12.7 |
| Paraffins and Naphthenes, vol. % | 87.3 |
| Pour Point, ° F. | 80 |

In each case, the light vacuum gas oil was processed with a reactor pressure of 2000 psig., a liquid hourly space velocity of 1.0, a hydrogen circulation rate of 9500 scf./bbl. and at a catalyst bed temperature which was required to yield a 315° F.+ product with a −5° F. pour point. Catalysts 1, 2 and 3 required catalyst temperatures of 763° F., 754° F. and 779° F., respectively, to yield the desired product characteristics. These data are presented in tabular form in Table II and in graphical form in the accompanying drawing.

TABLE II

| Evaluation For Hydrocracking Activity | | | |
|---|---|---|---|
| Catalyst Identity | 1 | 2 | 3 |
| Alumina Concentration | 40 | 50 | 63 |
| Reactor Temperature Required | | | |

TABLE II-continued

| Evaluation For Hydrocracking Activity | | | |
|---|---|---|---|
| Catalyst Identity | 1 | 2 | 3 |
| For −5° F. Pour Point | 763 | 754 | 779 |

From the data presented in foregoing Table I and with reference to the accompanying drawing, it will be seen that the three catalysts' increasing concentrations of alumina in the carrier material, the latter ranging from 40% to 63% by weight, did not produce normally liquid hydrocarbon products with improved pour point characteristics at the lowest catalyst bed temperature. This is clearly brought out upon comparing the results obtained through the use of catalysts 1, 2 and 3 which results in catalyst bed temperatures of 763° F., 754° F. and 779° F., respectively, for the desired product characteristics. Datum points 1, 2 and 3 in the drawing are representative of the results obtained with catalysts 1, 2 and 3 respectively. These data were employed in preparing curve 4 of the drawing, which curve clearly illustrates the criticality attached to an alumina concentration within the range of about 43% to about 57% by weight, in order to produce a liquid product with the desired characteristics at the lowest catalyst bed temperature. The additional economic advantages afforded through this particular result will be readily recognized by those possessing skill within the art of petroleum refining processes.

Specific operating conditions, processing techniques, particular catalytic composites and other individual process details will be given in the following detailed description of several of the hydrocarbon hydroprocesses to which the present invention is applicable. These will be presented by way of examples given in conjunction with commercially-scaled operating units. In presenting these examples, it is not intended that the invention be limited to the specific illustrations, nor is it intended that a given process be limited to the particular operating conditions, catalytic composite, processing techniques, charge stocks, etc. It is understood, therefore, that the present invention is merely illustrated by the specifics hereinafter set forth.

EXAMPLE II

In this example, the present invention is illustrated as applied to the hydrogenation of aromatic hydrocarbons such as benzene, toluene, the various xylenes, naphthalenes, etc., to form the corresponding cyclic paraffins. When applied to the hydrogenation of aromatic hydrocarbons, which are contaminated by sulfurous compounds, primarily thiphenic compounds, the process is advantageous in that it affords 100.0% conversion without the necessity for the substantially complete prior removal of the sulfur compounds. The corresponding cyclic paraffins, resulting from the hydrogenation of the aromatic nuclei, include compounds such as cyclohexane, mono-, di-, tri-substituted cyclohexanes, decahydronaphthalene, tetrahydronaphthalene, etc., which find widespread use as a variety of commercial industries in the manufacture of nylon, as solvents for various fats, oils, waxes, etc.

Aromatic concentrates are obtained by a multiplicity of techniques. For example, a benzene-containing fraction may be subjected to distillation to provide a heart-cut which contains the benzene. This is then subjected to a solvent extraction process which separates the benzene from the normal or iso-paraffinic components, and the naphthenes contained therein. Benzene is readily recovered from the selected solvent by way of distillation, and in a purity of 99.0% or more. Heretofore, the hydrogenation of aromatic hydrocarbons, for example benzene, has been effected with a nickel-containing catalyst. This extremely disadvantageous in many respects, and especially from the standpoint that nickel is quite sensitive to the minor quantity of sulfurous compounds which may be contained in the benzene concentrate. In accordance with the present process, the benzene is hydrogenated in contact with a catalytic composite comprising a 50/50 silica-alumina carrier material and containing 8 weight percent nickel and 18 weight percent tungsten. Operating conditions include a maximum catalyst bed temperature in the range of about 200° F. to about 800° F., a pressure of from 500 to about 2,000 psig., a liquid hourly space velocity of about 1.0 to about 10.0 and a hydrogen circulation rate in an amount sufficient to yield a mole ratio of hydrogen to cyclohexane, in the product effluent from the last reaction zone, not substantially less than about 4.0:1. Although not essential, one preferred operating technique involves the use of three reaction zones, each of which contains approximately one-third of the total quantity of catalyst employed. The process is further facilitated when the total fresh benzene is added in three approximately equal portions, one each to the inlet of each of the three reaction zones.

The hydrogenation process will be described in connection with a commercially-scaled unit having a total fresh benzene feed capacity of about 1,488 barrels per day. Makeup gas in an amount of about 741.6 mols/hr. is admixed with 2,396 Bbl./day (about 329 mols/hr.) of a cyclohexane recycle stream, the mixture being at a temperature of about 137° F., and further mixed with 96.24 mols/hr. (582 Bbl./day) of the benzene feed; the final mixture constitutes the total charge to the first reaction zone.

Following suitable heat-exchange with various hot effluent streams, the total feed to the first reaction zone is at a temperature of 385° F. and a pressure of 460 psig. The reaction zone effluent is at a temperature of 606° F. and a pressure of about 450 psig. The total effluent from the first reaction zone is utilized as a heat-exchange medium, in a steam generator, whereby the temperature is reduced to a level of about 545° F. The cooled effluent is admixed with about 98.5 moles per hour (596 Bbl./day) of fresh benzene feed, at a temperature of 100° F.; the resulting temperature is 400° F., and the mixture enters the second reaction zone at a pressure of about 440 psig. The second reaction zone effluent, at a pressure of 425 psig. and a temperature of 611° F., is admixed with 51.21 mols/hr. (310 Bbl./day) of fresh benzene feed, the resulting mixture being at a temperature of 578° F. Following its use as a heat-exchange medium, the temperature is reduced to 400° F., and the mixture enters the third reaction zone at a pressure of 415 psig. The third reaction zone effluent is at a temperature of about 500° F. and a pressure of about 400 psig. Through utilization as a heat-exchange medium, the temperature is reduced to a level of about 244° F., and subsequently reduced to a level of about 115° F. by use of an air-cooled condenser. The cooled third reaction zone effluent is introduced into a high pressure separator, at a pressure of about 370 psig.

A hydrogen-rich vaporous phase is withdrawn from the high pressure separator and recycled by way of compressive means, at a pressure of about 475 psig., to the inlet of the first reaction zone. A portion of the normally liquid phase is recycled to the first reaction zone as the cyclohexane concentrate hereinbefore described. The remainder of the normally liquid phase is passed into a stabilizing column functioning at an operating pressure of about 250 psig., a top temperature of about 160° F. and a bottom temperature of about 430° F. The cyclohexane product is withdrawn from the stabilizer as a bottoms stream, the overhead stream being vented to fuel. The cyclohexane concentrate is recovered in an amount of about 245.80 moles per hour, of which only about 0.60 moles per hour constitutes other hexanes. In brief summation, of the 19,207 pounds per hour of fresh benzene feed, 20,685 pounds per hour of cyclohexane product is recovered.

EXAMPLE III

Another hydrocarbon hydroprocessing scheme, to which the present invention is applicable, involves the hydrorefining of coke-forming hydrocarbon distillates. The hydrocarbon distillates are generally sulfurous in nature, and contain mono-olefinic, di-olefinic and aromatic hydrocarbons. Through the utilization of a catalytic composite prepared according to the present invention increased selectivity and stability of operation is obtained; selectively is most noticeable with respect to the retention of aromatics, and in hydrogenating conjugated di-olefinic and mono-olefinic hydrocarbons. Such charge stocks generally result from diverse conversion processes including the catalytic and/or thermal cracking of petroleum, sometimes referred to as pyrolysis, the destructive distillation of wood or coal, shale or retorting, etc. The impurities in these distillate fractions must necessarily be removed before the distillates are suitable for their intended use, or which when removed, enhance the value of the distillate fraction for further processing. Frequently, it is intended that these charge stocks be substantially desulfurized, saturated to the extent necessary to remove the conjugated di-olefins, while simultaneously retaining the aromatic hydrocarbons. When subjected to hydrorefining for the purpose of removing the contaminating influences, there is encountered difficulty in effecting the desired degree of reaction due to the formation of coke and other carbonaceous material.

As utilized herein, "hydrogenating" is intended to be synonymous with "hydrorefining". The purpose is to provide a highly selective and stable process for hydrogenating coke-forming hydrocarbon distillates, and this is accomplished through the use of a fixed-bed catalytic reaction system utilizing a catalyst of the present invention. There exists two separate, desirable routes for the treatment of coke-forming distillates, for example a pyrolysis naphtha by-product. One such route is directed toward a product suitable for use in certain gasoline blending. With this as the desired object, the process can be effected in a single stage, or reaction zone, with the catalytic composite hereinafter specifically described as the first-stage catalyst. The attainable selectivity in this instance resides primarily in the hydrogenation of highly reactive double bonds. In the case of conjugated di-olefins, the selectivity afforded restricts the hydrogenation to produce mono-olefins, and, with respect to the styrenes, for example, the hydrogenation is inhibited to produce alkyl benzenes without "ring" saturation. The selectivity is accomplished with a minimum of polymer formation either to "gums", or lower molecular weight polymers which would necessitate a re-running of the product before blending to gasoline would be feasible. Other advantages of restricting the hydrogenating of the conjugated di-olefins, such as 1,5 normal hexadiene are not usually offensive in suitably inhibited gasolines in some locales, and will not react in this first stage. Some fresh charge stocks are sufficiently low in mercaptan sulfur content that direct gasoline blending may be considered, although a mild treatment for mercaptan sulfur removal might be necessary. These considerations are generally applicable to foreign markets, particularly European, where olefinic and sulfur-containing gasolines are not too objectionable. It must be noted that the sulfurous compounds, and the mono-olefins, whether virgin, or products of di-olefin partial saturation, are unchanged in the single, or first-stage reaction zone. Where however the desired end result is aromatic hydrocarbon retention, intended for subsequent extraction, the two-stage route is required. The mono-olefins must be substantially saturated in the second stage to facilitate aromatic extraction by way of currently utilized methods. Thus, the desired necessary hydrogenation involves saturation of the mono-olefins, as well as sulfur removal, the latter required for an acceptable ultimate aromatic product. Attendant upon this is the necessity to avoid even partial saturation of aromatic nuclei.

With respect to one catalytic composite, its principal function involves the selective hydrogenation of conjugated di-olefinic hydrocarbons to mono-olefinic hydrocarbons. The particular catalytic composite possesses unusual stability notwithstanding the presence of relatively large quantities of sulfurous compounds in the fresh charge stock. The catalytic composite comprises a 50/50 silica-alumina carrier material and containing 8 weight percent nickel, 18 weight percent tungsten and an alkali-metal component, the latter being preferably potassium and/or lithium. It is especially preferred, for use in this particular hydrocarbon hydroprocessing scheme, that the catalytic composite be substantially free from any "acid-acting" propensities. The catalytic composite, utilized in the second reaction zone for the primary purpose of effecting the destructive conversion of sulfurous compounds into hydrogen sulfide and hydrocarbons, is a composite similar to the first reaction zone catalyst without an alkali metal component. Through the utilization of a particular sequence of processing steps, and the use of the foregoing described catalyst composites, the formation of high molecular weight polymers and co-polymers is inhibited to a degree which permits processing for an extended period of time. Briefly, this is accomplished by initiating the hydrorefining reactions at temperatures below about 500° F., at which temperatures the coke-forming reactions are not promoted. The operating conditions within the second reaction zone are such that the sulfurous compounds are removed without incurring the detrimental polymerization reactions otherwise resulting were it not for the saturation of the conjugated di-olefinic hydrocarbons within the first reaction zone.

The hydrocarbon distillate charge stock, for example, a light naphtha by-product from a commercial cracking unit designed and operated for the production of ethylene, having a gravity of about 34.0° API, a bromine number of about 35.0, a diene value of about 17.5 and containing about 1,600 ppm. by weight of sulfur and 75.9 vol.% aromatic hydrocarbons, is admixed with recycled hydrogen. This light naphtha co-product has an initial boiling point of about 164° F. and an end boiling point of about 333° F. The hydrogen circulation rate is within the range of from about 1,000 to about 10,000 scf./bbl., and preferably in the narrower range of from 1,500 to about 6,000 scf./bbl. The charge stock is heated to a temperature such that the maximum catalyst temperature is in the range of from about 200° F. to about 500° F., by way of heat-exchange with various product effluent streams, and is introduced into the first reaction zone at an LHSV in the range of about 0.5 to about 10.0. The reaction zone is maintained at a pressure of from 400 to about 1,000 psig., and preferably at a level in the range of from 500 psig. to about 900 psig.

The temperature of the product effluent from the first reaction zone is increased to a level above about 500° F., and preferably to result in a maximum catalyst temperature in the range of 600° F. to 900° F. When the process is functioning efficiently, the diene value of the liquid charge entering the second catalytic reaction zone is less than about 1.0 and often less than about 0.3. The conversion of nitrogenous and sulfurous compounds, and the saturation of mono-olefins, contained within the first zone effluent, is effected in the second zone. The second catalytic reaction zone is maintained under an imposed pressure of from about 400 to about 1,000 psig., and preferably at a level of from about 500 to about 900 psig. The two-stage process is facilitated when the focal point for pressure control is the high pressure separator serving to separate the product effluent from the second catalytic reaction zone. It will, therefore, be maintained at a pressure slightly less than the first catalytic reaction zone, as a result of fluid flow through the system. The LHSV through the second reaction zone is about 0.5 to about 10.0, based upon fresh feed only. The hydrogen circulation rate will be in a range of from 1,000 to about 10,000 scf./bbl., and preferably from about 1,000 to about 8,000 scf./bbl. Series-flow through the entire system is facilitated when the recycle hydrogen is admixed with the fresh hydrocarbon charge stock. Make-up hydrogen, to supplant that consumed in the overall process, may be introduced from any suitable external source, but is preferably introduced into the system by way of the effluent line from the first catalytic reaction zone to the second catalytic reaction zone.

With respect to the naphtha boiling range portion of the product effluent, the sulfur concentration is about 0.1 ppm., the aromatic concentration is about 75.1% by volume, the bromine number is less than about 0.3 and the diene value is essentially "nil".

With charge stocks having exceedingly high diene values, a recycle diluent is employed in order to prevent an excessive temperature rise in the reaction system. Where so utilized, the source of the diluent is preferably a portion of the normally liquid product effluent from the second catalytic reaction zone. The precise quantity of recycle material varies from feed stock to feed stock; however, the rate at any given time is controlled by monitoring the diene value of the combined liquid feed to the first reaction zone. As the diene value exceeds a level of about 25.0, the quantity of recycle is increased, thereby increasing the combined liquid feed ratio; when the diene value approaches a level of about 20.0, or less, the quantity of recycle diluent may be lessened, thereby decreasing the combined liquid feed ratio.

With another so-called pyrolysis gasoline, having a gravity of about 36.4° API, containing 600 ppm. by weight of sulfur, 78.5% by volume of aromatics, and having a bromine number of 45 and a diene value of 25.5 it is initially processed in a first reaction zone containing a catalytic composite comprising a 50/50 silica-alumina carrier material and containing 8 weight percent nickel, 18 weight percent tungsten and 0.5 weight percent lithium. The fresh feed charge rate is 3,300 bbl./day, and this is admixed with 2,475 bbl./day of the normally liquid diluent. Based upon fresh feed only, the LHSV is 2.5 and the hydrogen circulation rate is 1,750 scf./bbl. The charge is raised to a temperature of about 250° F., and enters the first reaction zone at a pressure of about 850 psig. The product effluent emanates from the first reaction zone at a pressure of about 830 psig. and a temperature of about 350° F. The effluent is admixed with about 660 scf./bbl. of make-up hydrogen, and the temperature is increased to a level of about 545° F., the heated stream is introduced into the second reaction zone under a pressure of about 790 psig. The LHSV, exclusive of the recycle diluent, is 2.5, and the hydrogen circulation rate is about 1,500. The second reaction zone contains a catalyst comprising a 50/50 silica-alumina carrier material and containing 8 weight percent nickel and 18 weight percent tungsten. The reaction product effluent is introduced following its use as a heat-exchange medium and further cooling, to reduce its temperature from 620° F. to a level of 100° F., into a high-pressure separator at a pressure of about 750 psig. The normally liquid stream from the cold separator is introduced into a reboiled stripping column for hydrogen sulfide removal and depentanization. The hydrogen sulfide stripping column functions at conditions of temperature and pressure required to concentrate a $C_6$ to $C_9$ aromatic stream as a bottoms fraction. With respect to the overall product distribution, only 690 lbs/hr of pentanes and lighter hydrocarbons is indicated in the stripper overhead. The aromatic concentrate is recovered in an amount of about 40,070 lbs/hr (the fresh feed is 40,120 lbs/hr); these results are achieved with a hydrogen comsumption of only 660 scf./bbl. With respect to the desired product, the aromatic concentration is 78.0, the sulfur concentration is less than 1.0 ppm. by weight, and the diene value is essentially "nil".

EXAMPLE IV

This example is presented to illustrate still another hydrocarbon hydroprocessing scheme for the improvement of the jet fuel characteristics of sulfurous kerosene boiling range fractions. The improvement is especially noticeable in the IPT Smoke Point, the concentration of aromatic hydrocarbons and the concentration of sulfur. A two-stage process wherein desulfurization is effected in the first reaction zone at relatively mild severities which result in a normally liquid product effluent containing from about 15 to about 35 ppm. of sulfur by weight. Aromatic saturation is the principal reaction effected in the second reaction zone, having disposed therein a catalytic composite comprising a 50/50 silica-alumina carrier material and containing 8 weight percent nickel, 18 weight percent tungsten, and 0.6 weight percent combined chloride.

Suitable charge stocks are kerosene fractions having an initial boiling point as low as about 300° F., and an end boiling point as high as about 575° F., and, in some instances, up to 600° F. Examplary of such kerosene fractions are those boiling from about 300° F. to about 550° F., from 330° F. to about 500° F., from 330° F. to about 530° F., etc. As a specific example, a kerosene obtained from hydrocracking a Mid-continent slurry oil, having a gravity of about 30.5° API, an initial boiling point of about 388° F., an end boiling point of about 522° F., has an IPT Smoke Point of 17.1 mm., and contains 530 ppm. of sulfur and 24.8% by volume of aromatic hydrocarbons. Through the use of the catalytic process of the present invention, the improvement in the jet fuel quality of such a kerosene fraction is most significant with respect to raising the the IPT Smoke Point, and reducing the concentration of sulfur and the quantity of aromatic hydrocarbons. Specifications regarding the poorest quality of jet fuel, commonly referred to as Jet A, Jet-A1 and Jet-B call for a sulfur concentration of about 0.3% by weight maximum (3,000 ppm.), a minimum IPT Smoke Point of 25 mm. and a maximum aromatic concentration of about 20.0 vol.%.

The charge stock is admixed with circulating hydrogen in an amount within the range of from about 1,000 to about 2,000 scf./bbl. This mixture is heated to a temperature level necessary to control the maximum catalyst bed temperature below about 750° F., and preferably not above 700° F., with a lower catalyst bed temperature of about 600° F. The catalyst, a well known standard desulfurization catalyst containing about 2.2% by weight of cobalt and about 5.7% by weight of molybdenum, composited with alumina is disposed in a reaction zone maintained under an imposed pressure in the range of from about 500 to about 1,000 psig. The LHSV is in the range of about 0.5 to about 10.0, and preferably from about 0.5 to about 5.0. The total product effluent from this first catalytic reaction zone is separated to provide a hydrogen-rich gaseous phase and a normally liquid hydrocarbon stream containing 15 ppm. to about 35 ppm. of sulfur by weight. The normally liquid phase portion of the first reaction zone effluent is utilized as the fresh feed charge stock to the second reaction zone. In this particular instance, the first reaction zone decreases the sulfur concentration of about 25 ppm., the aromatic concentration to about 16.3% by volume, and has increased the IPT Smoke Point to a level of about 21.5 mm.

The catalytic composite within the second reaction zone is described hereinabove. The reaction zone is maintained at a pressure of about 400 to about 1,500 psig., and the hydrogen circulation rate is in the range of 1,500 to about 10,000 scf./bbl. The LHSV, hereinbefore defined, is in the range of from about 0.5 to about 5.0, and preferably from about 0.5 to about 3.0. It is preferred to limit the catalyst bed temperature in the second reaction zone to a maximum level of about 750° F. With a catalyst of this particular chemical and physical characteristics, optimum aromatic saturation, processing a feed stock containing from about 15 to about 35 ppm. of sulfur, is effected at maximum catalyst bed temperatures in the range of about 625° F. to about 750° F. With respect to the normally liquid kerosene fraction, recovered from the condensed liquid removed from the total product effluent, the sulfur concentration is effectively "nil", being about 0.1 ppm. The quantity of aromatic hydrocarbons has been decreased to a level of about 0.75% by volume, and the IPT Smoke Point has been increased to about 36.3 mm.

EXAMPLE V

This illustration of a hydrocarbon hydroprocessing scheme, encompassed by my invention is one which involves hydrocracking heavy hydrocarbonaceous material into lower boiling hydrocarbon products. In this instance, the preferred catalysts contain a 50/50 silica-alumina carrier material, 8 weight percent nickel, 18 weight percent tungsten and 0.7 weight percent combined chloride.

Most of the virgin stocks, intended for hydrocracking, are contaminated by sulfurous compounds and nitrogenous compounds, and, in the case of the heavier charge stocks, various metallic contaminants, insoluble asphalts, etc. Contaminated charge stocks are generally hydrorefined in order to prepare a charge suitable for hydrocracking. Thus, the catalytic process of the present invention can be beneficially utilized as the second stage of a two-stage process, in the first stage of which the fresh feed is hydrorefined.

Hydrocracking reactions are generally effected at elevated pressures in the range of about 800 to about 5,000 psig., and preferably at some intermediate level of 1,000 to about 3,500 psig. Liquid hourly space velocities of about 0.25 to about 10.0 will be suitable, the lower range generally reserved for the heavier stocks. The hydrogen circulation rate will be at least about 3,000 scf./bbl., with an upper limit of about 50,000 scf./bbl., based upon fresh feed. For the majority of feed stocks, hydrogen circulation in the range of 5,000 to 20,000 scf./bbl. will suffice. With respect to the LHSV, it is based upon fresh feed, notwithstanding the use of recycle liquid providing a combined liquid feed ratio in the range of about 1.25 to about 6.0. The operating temperature again alludes to the temperature of the catalyst within the reaction zone, and is in the range of about 400° F. to about 900° F. Since the principal reactions are exothermic in nature, the increasing temperature gradient, experienced as the charge stock traverses the catalyst bed, results in an outlet temperature higher than that at the inlet to the catalyst bed. The maximum catalyst temperature should not exceed 900° F., and it is generally a preferred technique to limit the temperature increase to 100° F. or less.

Other possible constituent of the catalyst is a halogen component, either fluorine, chlorine, iodine, bromine, or mixtures thereof. Of these, it is preferred to utilize a catalyst containing fluorine and/or chlorine. The halogen component will be composited with the carrier material is such a manner as results in a final composite containing about 0.1% to about 1.5% by weight of halogen, calculated on an elemental basis.

A specific illustration of this hydrocarbon hydroprocessing technique involves the use of a catalytic composite hereinabove described.

This catalyst is intended for utilization in the conversion of 16,000 bbl./day of a blend of light gas oils to produce maximum quantities of a heptane-400° F. gasoline boiling range fraction. The charge stock has a gravity of 33.8° API, contains 0.19% by weight of sulfur (1,900 ppm.) and 67 ppm. by weight of nitrogen, and has an initial boiling point of 369° F., a 50% volumetric distillation temperature of 494° F. and an end boiling point of 655° F. The charge stock is initially subjected to a clean-up operation at maximum catalyst temperature of 750° F., a combined feed ratio of 1.0, an LHSV of 2.41 with a hydrogen circulation rate of about 500 scf./bbl. The pressure imposed upon the catalyst within the reaction zone is about 1,500 psig. Since at least a portion of the blended gas oil charge stock will be converted into a lower-boiling hydrocarbon product, the effluent from this clean-up reaction zone is separated to provide a normally liquid, 400° F.-plus charge for the hydrocracking reaction zone. The pressure imposed upon the second reaction zone is about 1,500 psig., and the hydrogen circulation rate is about 8,000 scf./bbl.

The original quantity of fresh feed to the clean-up reaction zone is about 16,000 bbl./day; following separation of the first zone effluent to provide the 400° F.-plus charge to the second reaction zone, the charge to the second reaction zone is in an amount of about 12,150 bbl./day, providing an LHSV of 0.85. The temperature at the inlet to the catalyst bed is 665° F., and a conventional hydrogen quench stream is utilized to maintain the maximum reactor outlet temperature at about 700° F. Following separation of the product effluent from the second reaction zone, to concentrate the desired gasoline boiling range fraction, the remaining 400° F.-plus normally liquid material, in an amount of 7,290 bbl./day, is recycled to the inlet of the second reaction zone, thus providing a combined liquid feed ratio thereto of about 1.60. In the following table, there is indicated the product yield and distribution of this process. With respect to normally liquid hydrocarbons, for convenience including butanes, the yields are given in vol.%; with respect to the normally gaseous hydrocarbons, ammonia and hydrogen sulfide, the yields are given in terms of wt. %. With respect to the first reaction zone, the hydrogen consumption is 1.31% by weight of the fresh feed (741 scf./bbl.), and for the hydrocracking reaction zone, 1.26% by weight of the fresh feed charge stock, or 713 scf./bbl.

TABLE

Hydrocracking Product Yield and Distribution

| Component | Stage I | Stage II | Total |
|---|---|---|---|
| Ammonia | 0.01 | — | 0.01 |
| Hydrogen Sulfide | 0.21 | — | 0.21 |
| Methane | 0.12 | 0.02 | 0.14 |
| Ethane | 0.22 | 0.40 | 0.62 |
| Propane | 1.03 | 3.48 | 4.51 |
| Butanes | 3.90 | 14.66 | 18.56 |
| Pentanes | 3.04 | 11.28 | 14.32 |
| Hexanes | 3.00 | 11.21 | 14.21 |
| $C_7$-400° F. | 18.85 | 49.56 | 68.41 |
| 400° F.-plus | 75.92* | — | — |

*Charge to Stage II

With respect to both the butanes product and pentane product, the former is indicated as being about 68.0% isobutane, while the latter constitutes about 93.0% isopentanes. An analysis of the combined pentane/hexane fraction indicates a gravity of 82.6° API, a clear research octane rating of 85.0 and a leaded research octane rating of 99.0; it will be noted that this constitutes an excellent blending component for motor fuel. The desired heptane-400° F. product indicates a gravity of 48.8° API, a clear research octane rating of 72.0 and a leaded research octane rating of 88.0. This gasoline boiling range fraction constitutes about 34.0% by volume paraffins, 36.0% by volume naphthenes and 30.0% by volume aromatic hydrocarbons. It will be recognized that this gasoline boiling range fraction constitutes an excellent charge stock for a catalytic reforming unit to improve the motor fuel characteristics thereof.

The foregoing specification, and particularly the examples, indicates the methods by which the present invention is effected, and the benefits afforded through the utilization thereof.

I claim as my invention:

1. A process for hydrocracking a hydrocarbonaceous charge stock into lower molecular weight hydrocarbons, which process comprises reacting said charge stock with hydrogen at hydrocracking conditions, and in contact with a catalytic composite consisting essentially of a combination of a nickel component, and a tungsten component with a silica-alumina carrier material wherein said carrier material is co-gelled silica-alumina consisting of from about 43 percent to about 57 percent by weight alumina and from about 57 to about 43 percent by weight silica and wherein said components are present in amounts sufficient to result in the composite containing on an elemental basis, about 2 to about 10 percent by weight of the nickel component and about 8 to about 20 percent by weight of the tungsten components, and separating the resulting reaction zone effluent to recover said lower molecular weight hydrocarbons.

2. The process of claim 1 further characterized in that said silica-alumina carrier material is crystalline.

3. The process of claim 1 further characterized in that said silica-alumina carrier material is faujasite.

* * * * *